United States Patent
Pazdur et al.

(10) Patent No.: US 11,634,376 B2
(45) Date of Patent: Apr. 25, 2023

(54) LONG ALPHA-OMEGA DI-FUNCTIONAL LINEAR ETHERS

(71) Applicant: UNIVERSITEIT ANTWERPEN, Antwerp (BE)

(72) Inventors: Lukasz Pazdur, Antwerp (BE); Serge M. F. Tavernier, Antwerp (BE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 182 days.

(21) Appl. No.: 16/979,976

(22) PCT Filed: Mar. 14, 2019

(86) PCT No.: PCT/EP2019/056493
§ 371 (c)(1),
(2) Date: Sep. 11, 2020

(87) PCT Pub. No.: WO2019/175352
PCT Pub. Date: Sep. 19, 2019

(65) Prior Publication Data
US 2021/0047255 A1 Feb. 18, 2021

(30) Foreign Application Priority Data
Mar. 14, 2018 (EP) .................................... 18161651

(51) Int. Cl.
| C07C 51/34 | (2006.01) |
| C07C 41/26 | (2006.01) |
| C07C 213/02 | (2006.01) |
| C07C 43/13 | (2006.01) |
| C07C 59/305 | (2006.01) |
| C07C 217/08 | (2006.01) |
| B01J 21/10 | (2006.01) |

(52) U.S. Cl.
CPC ............... *C07C 51/34* (2013.01); *B01J 21/10* (2013.01); *C07C 41/26* (2013.01); *C07C 213/02* (2013.01); *C07C 43/132* (2013.01); *C07C 59/305* (2013.01); *C07C 217/08* (2013.01)

(58) Field of Classification Search
CPC ..... C07C 59/305; C07C 43/132; C07C 45/40; C07C 51/285; C07C 41/01; C07C 41/26; C07C 51/245; C07C 68/06; C07C 47/198; C07C 217/08; C07C 43/15; C07C 51/34; C07C 69/96; C07C 213/02; B01J 21/10
USPC .......................................................... 564/503
See application file for complete search history.

(56) References Cited

FOREIGN PATENT DOCUMENTS

WO 200078937 A1 12/2000

OTHER PUBLICATIONS

International Search Report and Written Opinion dated Apr. 29, 2019 for Application No. PCT/EP2019/056493.
Extended European Search Report dated Sep. 11, 2018 for Application No. 18161651.7.
Osakada, et al., "Preparation of [alpha]. [omega] -Diols of Long Carbon Chains and Their Use in Polyurethane Synthesis", Bulletin of the Chemical Society of Japan, vol. 71, No. 6, Jun. 1, 1998.
Grubbs, et al., "The Development of $L_2X_2Ru$==CHR Olefin Metathesis Catalysts: An Organometallic Success Story", Accounts of Chemical Research, American Chemical Society, vol. 34, No. 1, pp. 18-29, 2001.
Santacesaria, et al., "Oxidative Cleavage of the Double Bond of Monoenic Fatty Chains in Two Steps: A New Promising Route to Azelaic Acid and Other Industrial Products", Ind. Eng. Chem. Res., vol. 39, No. 8, pp. 2766-2771, 2000.
Zibek, et al., "Fermentative Herstellund der a,w-Di-Carbonsaure 1,18-Oktadecendisäure als Grundbaustein für biobasierte Kunststoffe", Chemie Ingenier Technik, No. II, pp. 1797-1808, 2009.

*Primary Examiner* — Ana Z Muresan
(74) *Attorney, Agent, or Firm* — Dinsmore & Shohl, LLP

(57) ABSTRACT

The current invention relates to long α-ω di-functional linear molecules as building blocks closing the gap between small molecules and polymers, or in a polycondensated form, in the production of oligomers and/or polymers, surfactants, lubricants, coatings, colloidal stabilizing surface chains/molecules.

19 Claims, No Drawings

LONG ALPHA-OMEGA DI-FUNCTIONAL LINEAR ETHERS

FIELD OF THE INVENTION

The current invention relates to long α-ω di-functional linear molecules as building blocks closing the gap between small molecules and polymers, or in a polycondensated form, in the production of oligomers and/or polymers, surfactants, lubricants, coatings, colloidal stabilizing surface chains/molecules. The invention relates more specifically to long α-ω di-functional linear molecules where the functional groups are selected from the group comprising alcohol-, carboxylic acid- and amine-functionality.

BACKGROUND TO THE INVENTION

Long (i.e.=number of atoms in the main chain >10) di-functional (or even higher functional) molecules comprising alcohol and/or carboxylic acid and/or amine functionalities are increasingly interesting for new product development in general, especially if they can be made from renewable and/or bio-based starting products. They become even more interesting in case the functionalities are separated by an appreciable number of atoms in the chain, so that the molecule can be considered as having its functionalities in two distinct regions within the molecule.

Basic reason for said interest is that such long molecules can be used to make in a simple way even longer molecules by reaction of the at least two functional groups with each other or with appropriate other di-functional (or even high functional) molecules leading to oligomers and/or polymers. Depending on the general nature of the molecule (e.g. its hydrophobicity, flexibility, . . . ) applications of such longer molecules can be found in the field of lubrication, coatings, emulsifiers/stabilizers of dispersions, new designer plastics e.g. for 3D printing, etc.

A limited number of related short and mid-sized di-functional molecules can be found in nature (e.g. succinic acid, azelaic acid, 1,6 hexanediol, . . . ). Long di-functional materials are rare and often expensive (e.g. 12-OH stearic acid, . . . ). Also, the production of such type long molecules is difficult, expensive and has only moderate yield, which is for instance the case for 1,18 octadecanedioic acid prepared by metathesis using Grub's reagent (Grubbs et. al. 2001), intrinsically limited to 50% (the other 50% is side product). The preparation of such compounds using biotechnological methods is also complex and characterized by low yields. For example said 1,18 octadecanedioic acid can be obtained by ω-oxidation of oleic acid using micro-organisms such as e.g. *Candida tropicalis* ATCC20336 and genetic modified *Candida tropicalis* ATCC20962 (Ziebek et. al. 2009) and post hydrogenation to obtain the saturated carbon chain, which method is laborious and expensive. Also the nature of the natural according compounds and those obtained by the cited tedious methods is limited to only carbon atom containing chains between the functional groups. This reduces the flexibility to design and introduce additional properties in long di-functional molecules.

Thus, there is a clear need for new types of long (i.e.=number of atoms in the main chain >10) di-functional (or even higher functional) molecules that preferentially can be obtained from renewable and bio-based starting products, which is solved by the current invention.

SUMMARY OF THE INVENTION

The current invention relates to a compound of Formula I, $$R_1\text{-}L_1\text{-}O\text{-}L_1\text{-}R_2 \quad (I)$$

wherein
$L_1$ is $C_8$-alkyl;
$R_1$ and $R_2$ are each independently selected from —$(CH_2)_m$OH, —$(CH_2)_n$COOH, —$(CH_2)_p$NH$_2$;
each occurrence of m is independently an integer from 5 to 9;
each occurrence of n is independently an integer from 3 to 8;
each occurrence of p is independently an integer from 1 to 9; preferably from 5 to 9;
and wherein said compound is not HOOC—$(CH_2)_{15}$—O—$(CH_2)_{16}$—OH;

In a further embodiment, the compound is represented by Formula 1, wherein
$L_1$ is $C_8$-alkyl;
$R_1$ and $R_2$ are both selected from either —$(CH_2)_m$OH, —$(CH_2)_n$COOH, and —$(CH_2)_p$NH$_2$;
each occurrence of m is independently an integer from 5 to 9;
each occurrence of n is independently an integer from 3 to 8;
each occurrence of p is independently an integer from 1 to 9; preferably from 5 to 9.

In yet a further embodiment, the compound is represented by Formula I, wherein
$L_1$ is $C_8$-alkyl;
$R_1$ and $R_2$ are each selected from —$(CH_2)_m$OH, —$(CH_2)_n$COOH, —$(CH_2)_p$NH$_2$;
m is an integer from 5 to 9;
n is an integer from 3 to 8;
p is an integer from 1 to 9; preferably from 5 to 9;
and $R_1$ and $R_2$ are equal to each other.

In a preferred embodiment, the compound is selected from:

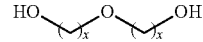

wherein x is an integer from 13 to 17;

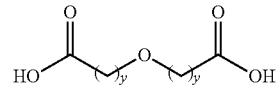

wherein y is an integer from 11 to 16;

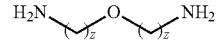

wherein z is an integer from 9 to 17; preferably from 13 to 17;

In another embodiment, the invention relates to a composition comprising a compound as described above.

In a certain embodiment, the compound and/or composition as described above is used in the production of oligomers and/or polymers, surfactants, lubricants, coatings, colloidal stabilizing surface chains/molecules.

In another embodiment, said invention relates to a method for the preparation of a compound of formula (II)

wherein
$L_3$ and $L_4$ are alkyl chains comprising at least 8 C atoms;
$R_3$ and $R_4$ are each independently selected from —OH, —COOH, —NH$_2$;
and wherein the total number of C atoms in $L_3$ and $R_3$ together and the total number of C atoms in $L_4$ and $R_4$ together is at most 17;
said method comprising the steps of:
  providing a first solution comprising at least one mono-unsaturated alcohol, dialkyl carbonate and a heterogeneous oxide based catalyst;
  heating the first solution;
  removing the catalyst and non-reacted dialkylcarbonate from the first solution, resulting in a second solution;
  adding a heterogeneous oxide based catalyst to said second solution, resulting in a third solution;
  heating said third solution to obtain an unsaturated dialkyl ether compound;
  cleaving the unsaturated bond of said unsaturated dialkyl ether to obtain functionalized end groups;
  optionally further derivatizing said obtained functional end groups;
  In a certain embodiment, said heterogeneous oxide based catalyst of the above-described method is a heterogeneous silicon/aluminum oxide based catalyst, more preferably a hydrotalcite.
  In another embodiment, the dialkyl carbonate of the above-described method is selected from a group comprising dimethylcarbonate and diethylcarbonate; In another embodiment, cleaving the unsaturated bond of the above-described method is performed by ozonolysis or by oxidation of the double bond. In a further embodiment, said ozonolysis is performed under oxidative or reductive conditions. In another embodiment; oxidation of the double bound results in a vicinal diol group wherein said vicinal diol group is oxidatively cleaved again.
  In a certain embodiment, optionally further derivatizing said obtained functional end groups of the above-described method comprises oxidation steps and/or reduction steps and/or the conversion of an alcohol group to an amine group; In another embodiment, the above-mentioned embodiments related to said method may be used for the preparation of the compounds of formula I.

DETAILED DESCRIPTION OF THE INVENTION

The current invention relates to a compound of Formula I, $$R_1\text{-}L_1\text{-}O\text{-}L_1\text{-}R_2 \qquad (I)$$

wherein
$L_1$ is $C_8$-alkyl;
$R_1$ and $R_2$ are each independently selected from —(CH$_2$)$_m$OH, —(CH$_2$)$_n$COOH, —(CH$_2$)$_p$NH$_2$;
each occurrence of m is independently an integer from 5 to 9;
each occurrence of n is independently an integer from 3 to 8;
each occurrence of p is independently an integer from 1 to 9; preferably from 5 to 9;
and wherein said compound is not HOOC—(CH$_2$)$_{15}$—O—(CH$_2$)$_{16}$—OH;

The compounds of the present invention are characterized in having a high tendency to crystallize, and resulting in a sufficiently high degree of crystallinity. This can be obtained in compounds having a sufficiently high melting point, such as about 70° C. or higher. Since the occurrence of an ether function (R—O—R') lowers the melting point of the molecules, a particular length of the alkyl chains ($L_1$-$R_1$ and $L_2$-$R_2$) is needed (to have a particular molecular weight) to increase the melting point. In case of carboxylic acid end-groups (—COOH) the molecular weight can be lower, due to the fact that the carboxyl group adds to the crystallization tendency. The consequence is that a lower range in chain length can be used in case of carboxylic end-groups.

As evident from the examples (see example 6), molecules with shorter chain length do not have the required melting point, i.e. HO—(CH2)9-O—(CH2)9-OH has a melting point of only 49.1° C., which is far less than the 70° C. as aimed for.

In a further embodiment, the compound is represented by Formula 1,
wherein
$L_1$ is $C_8$-alkyl;
$R_1$ and $R_2$ are both selected from either —(CH$_2$)$_m$OH, —(CH$_2$)$_n$COOH, and —(CH$_2$)$_p$NH$_2$;
each occurrence of m is independently an integer from 5 to 9;
each occurrence of n is independently an integer from 3 to 8;
each occurrence of p is independently an integer from 1 to 9 preferably from 5 to 9.

In yet a further embodiment, the compound is represented by Formula I,
wherein
$L_1$ is $C_8$-alkyl;
$R_1$ and $R_2$ are each selected from —(CH$_2$)$_m$OH, —(CH$_2$)$_n$COOH, —(CH$_2$)$_p$NH$_2$;
m is an integer from 5 to 9;
n is an integer from 3 to 8;
p is an integer from 1 to 9; preferably from 5 to 9;
and $R_1$ and $R_2$ are equal to each other.

In a preferred embodiment, the compound is selected from:

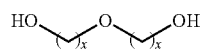

wherein x is an integer from 13 to 17;

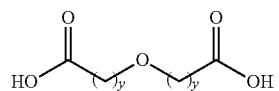

wherein y is an integer from 11 to 16;

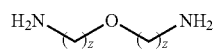

wherein z is an integer from 9 to 17; preferably from 13 to 17;

In a particular embodiment of the present invention, x may be an integer selected from 13, 14, 15, 16 and 17.

In another particular embodiment of the present invention, y may be an integer selected from 11, 12, 13, 14, 15 and 16.

In yet another particular embodiment of the present invention, z may be an integer selected from 13, 14, 15, 16 and 17.

In another embodiment, the invention relates to a composition comprising a compound as described above.

In a certain embodiment, the compound and/or composition as described above is used in the production of oligomers and/or polymers, surfactants, lubricants, coatings, colloidal stabilizing surface chains/molecules.

The term "oligomers" refers to a molecular complex of chemicals that comprises a few monomer units. Examples of oligomers include but are not limited to dimers, trimers and tetramers. In this invention, the term monomer can be any of the structures defined by formula I and formula II. The molecular complex can be the result by inter-reaction of said structures in the case they comprise functional groups that can interact or the molecular complex can be obtained by reaction of said structures with other molecules that can interact with the functional groups of said structures.

The term "polymers" refers to a molecular complex of chemicals that comprises a large number monomer units, typically larger than four.

The term "surfactants" refers to a surface active agent that lowers the surface tension (or interfacial tension) between a liquid and a gaseous phase, two liquids or between a liquid and a solid. Surfactants may include but are not limited to nonionic surfactants, anionic surfactants, cationic surfactants and zwitterionic surfactants.

The term "lubricants" refers to a substance, usually organic, introduced to reduce friction between surfaces in mutual contact, which ultimately reduces the heat generated when the surfaces move. It may also have the function of transmitting forces, transporting foreign particles, or heating or cooling the surfaces. Lubricants may include but are not limited to mineral oils, synthetic oils, solid lubricants, aqueous lubricants and biolubricants.

The term "coatings" refers to a covering that is applied to the surface of an object, usually referred to as the substrate. Coatings may include but are not limited to adhesive coatings, catalytic coatings, protective coatings, optical coatings, magnetic coatings and electrical coatings.

The term "colloidal stabilizing surface chains/molecules" refers to chains and molecules stabilizing the surface of a colloidal structure. A colloid is defined as a structure in which one substance of microscopically dispersed particles or liquid droplets is suspended throughout another substance. Colloidal stabilizing surface chains/molecules may include but are not limited to ionic groups comprising molecules and oligomeric molecules that have a tendency to adsorb at and or to interact chemically with the said surface of the dispersed particle or liquid droplet. Said molecules are characterized by the fact that they have at least one part with an affinity to the surface of the particle or droplet and a part with affinity to the surrounding substance. Preferentially said interacting part is positioned at one extremity of the said molecule. Typically, the molecular weight of said molecules is situated between 150 up to 15000 Dalton. Preferred interacting functional groups are selected from alcohols, carboxylic acid and amines.

In another embodiment, said invention relates to a method for the preparation of a compound of formula (II)

$$R_3\text{-}L_3\text{-}O\text{-}L_4\text{-}R_4 \quad\quad\quad (II)$$

Wherein
$L_3$ and $L_4$ are alkyl chains comprising at least 8 C atoms;
$R_3$ and $R_4$ are each independently selected from —OH, —COOH, —NH$_2$;
and wherein the total number of C atoms in $L_3$ and $R_3$ together and the total number of C atoms in $L_4$ and $R_4$ together is at most 17;
said method comprising the steps of:
  providing a first solution comprising at least one mono-unsaturated alcohol, dialkyl carbonate and a heterogeneous oxide based catalyst;
  heating the first solution;
  removing the catalyst and non-reacted dialkyl carbonate from the first solution, resulting in a second solution;
  adding a heterogeneous oxide based catalyst to said second solution, resulting in a third solution;
  heating said third solution to obtain an unsaturated dialkyl ether compound;
  cleaving the unsaturated bond of said unsaturated dialkyl ether to obtain functionalized end groups;
  optionally further derivatizing said obtained functional end groups;

In a certain embodiment, starting materials are fatty alcohols or derivatives thereof. Typical examples are oleyl alcohol and erucyl alcohol. They contain in their structure a double bond that can be used to introduce in the ether resulting from the condensation of the alcohols the functionalities that are targeted. Hence, the process is in fact a double step process:
  making the ether from the long chain alcohols
  modifying the functional groups present in both chains attached to the ether-oxygen In the case of oleyl alcohol and erucyl alcohol, the functional group is at the start a double bond. This double bond can then be modified to an alcohol, acid, amine, etc. . . . or cut whereby the resulting end of the chain is again functional (alcohol, acid, amine, etc. . . . ).

In order to make the ether, a classical Williamson method can be used. However, instead of this classical method to make an ether (Williamson method), surprisingly a green method to synthesize alkyl and aryl ethers out of fatty alcohols was found and optimized. The less effective Williamson method to make ethers is replaced by decarboxylation of dialkyl (or aryl alkyl) carbonates in the presence of a heterogeneous catalyst. In that way, alkyl and aryl ethers of fatty alcohols can be easily obtained.

In a certain embodiment, said heterogeneous oxide based catalyst of the above-described method is a heterogeneous silicon/aluminum oxide based catalyst, more preferably a hydrotalcite.

In another embodiment, the catalyst is conditioned before its use in a way to create on its surface the reactive groups enabling said ether formation.

In another embodiment said conditioning is realized by heating the catalyst to a predetermined temperature for a predetermined time.

In another embodiment, the dialkyl carbonate of the above-described method is selected from a group comprising dimethylcarbonate and diethylcarbonate.

In another embodiment, cleaving the unsaturated bond of the above-described method is performed by ozonolysis. Ozonolysis is an organic reaction wherein unsaturated bounds are reacted with ozone and subsequently cleaved by applying specific conditions. In a further embodiment, said ozonolysis is performed under oxidative or reductive conditions. When oxidative conditions are applied, said ozonolysis generates carboxylic acids. When reductive conditions are applied, said ozonolysis generates alcohols.

In another embodiment, cleaving the unsaturated bond of the above-described method is performed by oxidation of the double bond to a vicinal diol group and subsequent oxidative cleavage of the bond within the vicinal diol group to give alcohols.

In a certain embodiment, optionally further derivatizing said obtained functional end groups of the above-described method comprises oxidation and/or reduction and/or conversion of an alcohol group to an amine group.

In another embodiment, the above-mentioned embodiments related to said method may be used for the preparation of the compounds of formula I, $$R_1-L_1-O-L_1-R_2 \quad (I)$$

wherein
$L_1$ is $C_8$-alkyl;
$R_1$ and $R_2$ are each independently selected from —$(CH_2)_m$OH, —$(CH_2)_n$COOH, —$(CH_2)_p$NH$_2$;
each occurrence of m is independently an integer from 5 to 9;
each occurrence of n is independently an integer from 3 to 8;
each occurrence of p is independently an integer from 1 to 9; preferably from 5 to 9;
and wherein said compound is not HOOC—$(CH_2)_{15}$—O—$(CH_2)_{16}$—OH;
said method comprising the steps of:
 providing a first solution comprising at least one mono-unsaturated alcohol, dialkyl carbonate and a heterogeneous oxide based catalyst;
 heating the first solution;
 removing the catalyst and non-reacted dialkyl carbonate from the first solution, resulting in a second solution;
 adding a heterogeneous oxide based catalyst to said second solution, resulting in a third solution;
 heating said third solution to obtain an unsaturated dialkyl ether compound;
 cleaving the unsaturated bond of said unsaturated dialkyl ether to obtain functionalized end groups;
 optionally further derivatizing said obtained functional end groups;

In another embodiment, the same method using a heterogeneous catalyst and transesterification using dialkylcarbonates can be used to make the compounds as described by formula II ($R_3$-$L_3$-O-$L_4$-$R_4$) by coupling alcohol starting molecules comprising in their structure additionally to the said alcohol group either a —OH, —COOH or —NH$_2$ group or a functional group that after derivatization can give raise to a —OH, —COOH or —NH$_2$ group.

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 40 carbon atoms, more preferably 8 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$ alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers, . . . . For example, $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "alcohol" by itself or as part of another substituent refers to a R—OH structure, wherein R is an alkyl group.

The term "carboxy" or "carboxyl" by itself or as part of another substituent refers to the group —$CO_2H$. Thus, a carboxyalkyl is an alkyl group as defined above having at least one substituent that is —$CO_2H$.

The term "carbonate" refers to a

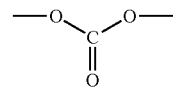

structure;
The term "dialkyl ether" refers to a

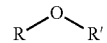

structure wherein R and R' are both alkyl groups.
The term "amine" refers to a —NH$_2$;
Whenever used in the present invention the term "compounds of the invention" or a similar term is meant to include the compounds of general Formula I and II. This term also refers to the compounds as depicted in claim 4, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

The invention will now be illustrated by means of the following examples, which do not limit the scope of the invention in any way.

Example 1 (Method to Synthesize α,ω Di-Functional Compounds Starting from Erucyl Alcohol (1) Using a First Hydrotalcite Based Approach)

The method is schematically shown in scheme 1. The decarboxylation of carbonates allows synthesizing long chain symmetrical unsaturated dialkyl ethers, such as for example dierucyl ether (2). The unsaturated long molecule can subsequently be ozonized and reduced to obtain long chain α,ω bifunctional dialkyl ether diol (3) or oxidized to obtain dialkyl ether diacid (4) with high yield. Dialkyl ether diol can be further converted into dialkyl ether diamine (5) (Scheme 1). The alternative method to obtain compound 3 is the synthesis of vicinal diols with pertungstic acid followed by oxidative cleavage of the carbon-carbon bond of diols with oxygen in the presence of cobalt acetate at high pressure. The first step of this reaction is the Prilezhaev (Prileschajew) reaction which is a convenient reaction to transform alkenes into epoxides or glycols (diols). This is achieved by means of an organic peracid in a neutral organic medium. Other names have been the Prilezhaev epoxidation, or simply the Prilezhaev oxidation. However, although said Prilezhaev reaction usually gives good quantitative yields, it is highly dependent on both the peracid used and the number and nature of groups attaching to the olefinic double bond. The Prilezhaev reaction is tolerable for many functional groups such as aromatic rings, esters and ethers. The pertungstic acid can be generated, for example, in situ by the reaction of hydrogenperoxyde with tungstic acid. The second step is the oxidative cleavage with molecular oxygen of the diol formed in the first step, in the presence of catalyst e.g. cobalt acetate (Santacesaria et al., 2000).

Example 2 (Comparison of Two Different Hydrotalcite Based Approaches to Make Dialkyl Ethers and Thereof Derived α,ω Di-Functional Compounds and Comparison with the Williamson Based Approach to Make the Similar Compounds)

Dierucyl ether (2) can be synthesized via a decarboxylation of a dialkyl carbonate in two ways. As presented in Scheme 2, route A requires only two steps: (i) synthesis of methyl erucyl carbonate and (ii) decarboxylation. The total yield of this approach is 67% (of isolated product). Route B gave better yield (Y=92%), but requires three steps: (i) synthesis of methyl erucyl carbonate, (ii) synthesis of dierucyl carbonate and (iii) decarboxylation.

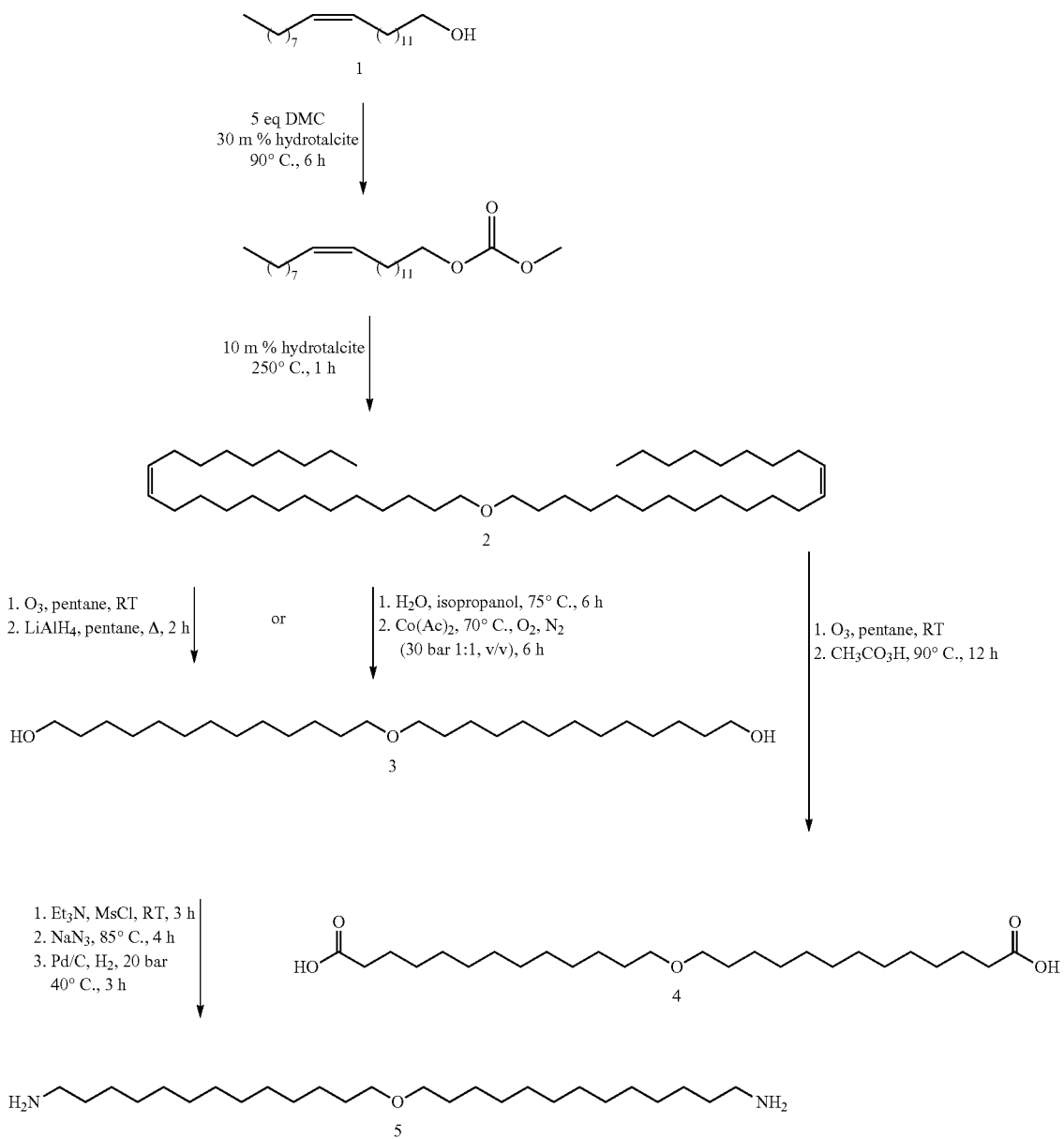

Scheme 2: Synthesis of dierucyl ether by decarboxylation of carbonate ester

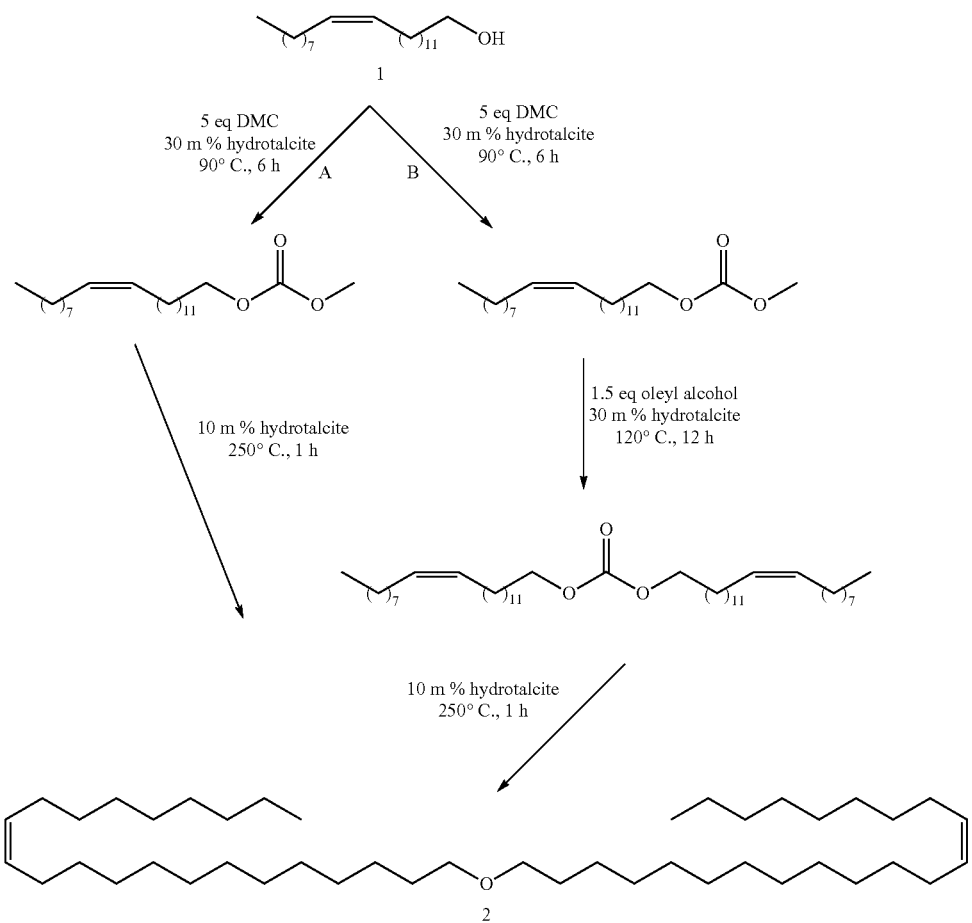

In route A, less steps are required to obtain the target molecule, but as side products methyl erucyl ether (25%) and erucyl alcohol (8%) are produced.

In route B more steps are required, but the total yield is higher and as side product only erucyl alcohol is produced (8%), which can be reused. After each step in the carbonate synthesis sequence a separation is required. After synthesis of methyl erucyl carbonate, the excess of dimethyl carbonate (DMC) needs to be removed—this can be done on a rotary evaporator (b.p. of DMC—90° C.). After synthesis of dierucyl carbonate, the excess of erucyl alcohol needs to be removed. This process can be done by distillation under reduced pressure (180° C. to 190° C.—1 mbar). The removal of the alcohol is very important in order to reduce the amount of side product after decarboxylation. The comparison of both routes is given in Table 1.

TABLE 1

The comparison of the two routes to synthesize dierucyl ether by decarboxylation of the corresponding dialkyl carbonate

| | Factors | Route A | Route B |
|---|---|---|---|
| 1 | Yield | 67% | 92% |
| 2 | # steps | 2 | 3 |
| 3 | Required purification | Yes, after $2^{nd}$ step | Yes, after $2^{nd}$ and $3^{rd}$ step |

TABLE 1-continued

The comparison of the two routes to synthesize dierucyl ether by decarboxylation of the corresponding dialkyl carbonate

| | Factors | Route A | Route B |
|---|---|---|---|
| 4 | Time | $1^{st}$ step 3 h | $1^{st}$ step 3 h |
| | | $2^{nd}$ step 30 minutes | $2^{nd}$ step 12 h |
| | | | $3^{rd}$ step 30 minutes |
| 5 | Recycle of side products | No - mixture of erucyl alcohol and methyl erucyl ether | Yes - only erucyl alcohol as side product |

By combining the decarboxylation method and ozonolysis, long chain α,ω bifunctional compounds can be obtained with high yields in a sustainable way. The overall yield of 13,13'-oxybis(tridecan-1-ol) (3) is 63% when route A is used. Using route B, a yield of 86.5% was obtained. When using a classical Williamson-based method (involving sulfonate as leaving group) to synthesize dierucyl ether and subsequently ozonizing the unsaturated ether, the total yield was found to be 38%.

Example 3 (Synthesis of
13,13'-oxybis(tridecan-1-ol) (3)

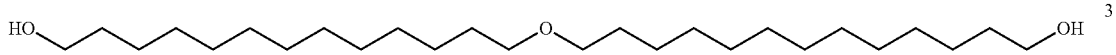 [SMILES: OCCCCCCCCCCCCCOCCCCCCCCCCCCCO]

Step 1: 290 g (1 eq) of erucyl alcohol and 402 mL (5 eq) of DMC were mixed at 90° C. After mixing, 87 g of hydrotalcite (30 m % regarding to the mass of alcohol) (calcinated at 800° C. for 5 h) was added and reaction was left for six hours. After reaction, the catalyst was centrifuged and the excess of DMC was removed with the use of rotavapor. Methyl erucyl carbonate was obtained in 100% yield.

Step 2: 33.2 g (10 m %) of hydrotalcite was placed into the Parr reactor and then heated to temperature 250° C. During the heating, the Parr reactor was flushed with argon. When the reactor reached the temperature of about 250° C., the balloon with argon was removed and the 332 g of methyl erucyl carbonate was added. The reaction was carried out about 1 h. After reaction, the mixture was centrifuged in order to remove the catalyst. In the last step, the mixture of dierucyl ether and methyl erucyl ether was separated by vacuum distillation in 195° C. (around 1 mbar). Dierucyl ether was isolated in 67% yield, as a residue after distillation.

Step 3: 55.1 g of dierucyl ether (1 eq) and about 150.0 mL of heptane were mixed with magnetic stirrer. A small amount of Sudan III, as the indicator of the reaction progress (red→yellow). The reaction was carried out sixteen hours with ozone until mixture had changed the color to yellow.

Step 4: 55.1 g (1 eq) of the product after ozonolysis and about 300 mL of dry heptane were mixed in three-neck bottom flask which was placed in ice bath. After mixing, 12.6 g (1.5 eq) of LiAlH$_4$ was added. During the reaction the flask was flushed with argon. The reaction was carried out about 2 h with at 40° C. Next, the reaction mixture was cooled down in an ice bath and 10 mL of cold water was dropwise added to neutralize not reacted LiAlH$_4$. In a next step 250 mL of 20 m % sulphuric acid was added to dissolve the solid part (LiOH and Al(OH)$_3$). The mixture was left over night and two layers were separated. The water layer was extracted with MTBE (2×150 mL). The organic layers were combined, dried with magnesium sulfate, filtrated and evaporated. The oil in the flask was mixed with petroleum ether and left over night in the freezer for crystallization. After the night mixture was centrifuged, the supernatant was moved to another flask and the solid phase was mixed with fresh cold petroleum ether and after 1 hour in the fridge centrifuged again. The white powder was filtrated and rinse a few times with cold petroleum ether. The 13,13'-oxybis (tridecan-1-ol) (3) was isolated in 84% yield.

The purity of the product was verified using H-NMR and the purity was found to be better than 97%. The melting point was 71.5° C. The melting point was measured with the Büchi B-545 apparatus, using visual observation of the melting process in a capillary tube. A first screening of the melting point temperature was done at a gradient of 1° C./min. The final measurement was done with a gradient of 0.1° C./min Example 4 (Synthesis of 13,13'-oxyditridecanoic acid (4))

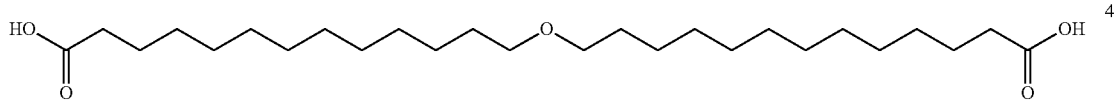 [SMILES: O=C(O)CCCCCCCCCCCCOCCCCCCCCCCCCC(=O)O]

Steps 1, 2 and 3 are identical as for synthesis of compound 3 (example 3).

Step 4: 40 g (1 eq) of the product after ozonolysis and 286.8 g (20 eq) of 35% solution of peracetic acid were mixed and the reaction was carried out about 20 h with reflux at 90° C. After reaction, the acetic acid was evaporated with the use of Rotavapor. The oil in the flask was mixed with petroleum ether and left over night in the fridge for crystallization. After night the mixture was centrifuged—the petroleum ether layer was moved to another flask an the solid phase was mixed with fresh petroleum ether and after 1 hour in the fridge centrifuged again. The white powder was filtrated and rinsed a few times with cold petroleum ether. The 13,13'-oxyditridecanoic acid (4) was isolated in 60% yield.

The purity of the product was verified using H-NMR and the purity was found to be better than 96%. The melting point was 81.0° C. The melting point was determined according to the method as defined in example 4.

Example 5 (Synthesis of 13,13'-oxybis(tridecan-1-amine) (5))

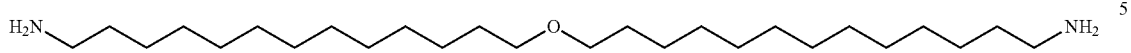 [SMILES: NCCCCCCCCCCCCCOCCCCCCCCCCCCCN]

The procedure to obtain 13,13'-oxybis(tridecan-1-ol) (3) was followed.

Step 1: In a two-necked round bottomed flask 30 g of compound 3 (1 eq) and 51 g of triethylamine (5 eq) were dissolved in 400 ml of THF at 50° C. To this solution, 39 g of mesyl chloride (3.4 eq) was slowly added via a syringe. The resulting yellow suspension was stirred for 3 h until it turned red. After addition of dichloromethane (150 mL), the reaction mixture was successively washed with water (100 mL), 2 M HCl (100 mL), water (100 mL), saturated NaHCO$_3$ solution (80 mL) and water (100 mL). The organic phase was dried with MgSO$_4$, and the solvent was removed in vacuo. After recrystallization from ethanol, 1-(methylsulfonyl)-13-((13-(methylsulfonyl)tridecyl)oxy)tridecane was obtained in 87% yield.

Step 2: In a round bottomed flask 37 g of 1-(methylsulfonyl)-13-((13-(methylsulfonyl)tridecyl)oxy)tridecane (1 eq) was dissolved in DMF (60 mL) at 65° C. To this solution was added 26 g of sodium azide (5 eq). The resulting mixture was stirred at 85° C. for 4 h. After cooling, the suspension water (50 mL) was added. The DMF water phase was extracted with hexane twice. The organic layer was successively washed with saturated $NaHCO_3$ solution (20 mL) and saturated NaCl solution (20 mL). The organic layer was dried with $MgSO_4$ and the solvent was removed in vacuo to give 1-azido-13-((13-azidotridecyl)oxy)tridecane as a white solid in 90% yield.

Step 3: 25 g of 1-azido-13-((13-azidotridecyl)oxy)tridecane (1 eq) and 2.5 g of Pd/C (10 wt %) (0.032 eq Pd) were weighed under air into a dry Schlenk tube. In an argon counter stream dry and degassed THF (70 mL) was added. The resulting mixture was cannula-transferred into a stainless steel mechanically stirred pressure reactor equipped with a glass inlay and a heating/cooling jacket controlled by a thermocouple dipping into the reaction mixture, which was purged several times with argon prior to the reaction. The reactor was closed and pressurized with 20 bar hydrogen and heated to 40° C. After 3 h, the reactor was cooled to room temperature and vented. The reaction mixture was then filtrated repeatedly over a Buchner funnel at 50° C. to remove catalyst residues. The solvent was removed in vacuo to afford an off-white solid, which was recrystallized from ethanol to give 13,13'-oxybis(tridecan-1-amine) (5) in 83% yield.

The purity of the product was verified using H-NMR and the purity was found to be 86%. A melting range was observed from 69-71° C. The melting point was determined according to the method as defined in example 4.

Example 6—Comparative Example (Synthesis of 9,9'-oxybis(nonan-1-ol))

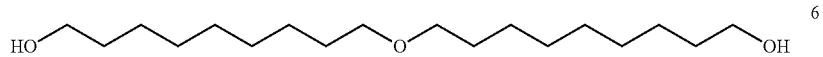 [SMILES: OCCCCCCCCCOCCCCCCCCCO]

Steps 1, 2, 3 and 4 are identical as for synthesis compound 3 (example 3) with one exception that oleyl alcohol was used as the starting material instead of erucyl alcohol. The 9,9'-oxybis(nonan-1-ol) (6) was isolated in 84% yield. White powder. The structure was verified using H-NMR and the purity was confirmed to be larger than 97%. The melting point was found to be 49.1° C. The melting point was determined according to the method as defined in example 4.

REFERENCES

Ziebek, S.; Huf, S.; Wagner, W.; Hirth, T.; Rupp, S., *Chem. Ing. Tech.* 2009, 81, 1797-1808

Grubbs, R. H.; Trnka, T. M., *Acc. Chem. Res.* 2001 34, 18-29

Santacesaria, E.; Sorrentino, A.; Rainone, F.; Di Serio, M.; Speranza, F., *Ind. Eng. Chem. Res.* 2000, 39, 2766-2771

The invention claimed is:

1. A compound of Formula I, $$R_1\text{-}L_1\text{-}O\text{-}L_1\text{-}R_2 \quad (I)$$

wherein $L_1$ is $C_8$-alkyl;

$R_1$ and $R_2$ are each independently selected from —$(CH_2)_m$OH, —$(CH_2)_n$COOH, and —$(CH_2)_p$NH$_2$;

each occurrence of m is independently an integer from 5 to 9;

each occurrence of n is independently an integer from 3 to 8;

each occurrence of p is independently an integer from 5 to 9; and the compound is not HOOC—$(CH_2)_{15}$—O—$(CH_2)_{16}$—OH.

2. The compound of claim 1, wherein $L_1$ is $C_8$-alkyl;

$R_1$ and $R_2$ are both selected from either —$(CH_2)_m$OH, or both —$(CH_2)_n$COOH, or both —$(CH_2)_p$NH$_2$;

each occurrence of m is independently an integer from 5 to 9;

each occurrence of n is independently an integer from 3 to 8;

each occurrence of p is independently an integer from 1 to 9; preferably from 5 to 9.

3. The compound of claim 1, wherein $L_1$ is $C_8$-alkyl;

$R_1$ and $R_2$ are both —$(CH_2)_m$OH, or both —$(CH_2)_n$COOH, or both —$(CH_2)_p$NH$_2$;

m is an integer from 5 to 9;

n is an integer from 3 to 8;

p is an integer from 5 to 9; and $R_1$ and $R_2$ are equal to each other.

4. The compound claim 1, selected from the group consisting of:

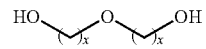

wherein each x is an identical integer from 13 to 17;

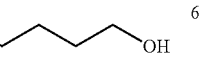

wherein each y is an identical integer from 11 to 16; and

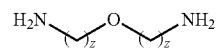

wherein each z is an identical integer from 13 to 17.

5. A composition comprising a compound according to claim 1.

6. The compound of claim 1, wherein $R_1$ and $R_2$ are each independently selected from —$(CH_2)_n$COOH and —$(CH_2)_p$NH$_2$.

7. The compound claim 1, selected from the group consisting of:

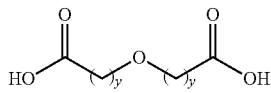

wherein each y is an identical integer from 11 to 16; and

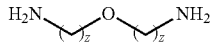

wherein each z is an identical integer from 13 to 17.

8. The compound of claim 1, wherein $R_1$ and $R_2$ are each —$(CH_2)_n$COOH.

9. The compound claim 1, selected from the group consisting of:

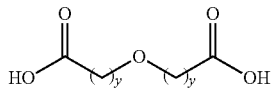

wherein each y is an identical integer from 11 to 16.

10. The compound of claim 1, having a melting point of at least 70° C.

11. A method for the preparation of a compound of formula (II)

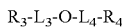    (II)

wherein
- $L_3$ and $L_4$ are alkyl chains comprising at least 8 C atoms;
- $R_3$ and $R_4$ are each independently selected from —OH, —COOH, —$NH_2$;
- the total number of C atoms in $L_3$ and $R_3$ together is at most 17; and
- the total number of C atoms in $L_4$ and $R_4$ together is at most 17, the method comprising:
- providing a first solution comprising at least one mono-unsaturated alcohol, dialkyl carbonate and a heterogeneous oxide based catalyst;
- heating the first solution;
- removing the catalyst and non-reacted dialkyl carbonate from the first solution, resulting in a second solution;
- adding a heterogeneous oxide based catalyst to the second solution, resulting in a third solution;
- heating the third solution to obtain an unsaturated dialkyl ether compound;
- cleaving the unsaturated bond of the unsaturated dialkyl ether to obtain functionalized end groups; and
- optionally further derivatizing the obtained functionalized end groups.

12. The method according to claim 11, wherein the heterogeneous oxide based catalyst is a heterogeneous silicon/aluminum oxide based catalyst.

13. The method according to claim 11 wherein the heterogeneous oxide based catalyst is hydrotalcite.

14. The method according to claim 11 wherein the dialkyl carbonate is selected from the group consisting of dimethylcarbonate and diethylcarbonate.

15. The method according to claim 11 wherein cleaving the unsaturated bond comprises performing ozonolysis.

16. The method according to claim 15, wherein the ozonolysis is performed under oxidative or reductive conditions.

17. The method according to claim 11 wherein cleaving the unsaturated bond comprises oxidizing the double bond resulting in a vicinal diol group wherein the vicinal diol group is oxidatively cleaved again.

18. The method according to claim 11, comprising further derivatizing the obtained functional end groups by oxidizing and/or reducing and/or converting an alcohol group to an amine group.

19. The method according to claim 11, wherein the compound of formula (II) is selected from the group consisting of

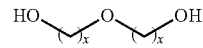

wherein each x is an identical integer from 13 to 17;

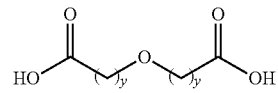

wherein each y is an identical integer from 11 to 16; and

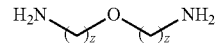

wherein each z is an identical integer from 13 to 17.

* * * * *

UNITED STATES PATENT AND TRADEMARK OFFICE
CERTIFICATE OF CORRECTION

PATENT NO. : 11,634,376 B2
APPLICATION NO. : 16/979976
DATED : April 25, 2023
INVENTOR(S) : Lukasz Pazdur and Serge M. F. Tavernier It is certified that error appears in the above-identified patent and that said Letters Patent is hereby corrected as shown below:

On the Title Page

In Column 2, item (56), other publications, cite no. 6, delete "a,w-Di-Carbonsaure" and insert --α,ω-Dicarbonsäure.--, therefor.

In the Specification

In Column 1, Line(s) 44, after "type", insert --of--.

In Column 5, Line(s) 25, after "number", insert --of--.

In Column 6, Line(s) 31, after "ether-oxygen", insert --.--.

In Column 9, scheme 1, delete "$H_2O$" and insert --$H_2O_2$--, therefor.

In Column 13, Line(s) 67, delete "rinse" and insert --rinsed--, therefor.

In Column 14, Line(s) 17, after "0.1° C./min", insert --.--.

In Column 14, Line(s) 38, delete "an" and insert --and--, therefor.

In the Claims

In Column 16, Line(s) 15, Claim 2, after "are both", delete "selected from either".

In Column 16, Line(s) 24, Claim 2, after "from", delete "1 to 9; preferably from".

In Column 16, Line(s) 32, Claim 4, after "compound", insert --of--.

Signed and Sealed this
Twenty-sixth Day of September, 2023

Katherine Kelly Vidal
*Director of the United States Patent and Trademark Office*

In Column 17, Line(s) 1, Claim 7, after "compound", insert --of--.

In Column 17, Line(s) 19, Claim 9, after "compound", insert --of--.